(12) United States Patent
Lewin et al.

(10) Patent No.: US 7,838,659 B2
(45) Date of Patent: Nov. 23, 2010

(54) HERPESVIRUS RIBOZYMES AND VECTORS

(75) Inventors: Alfred S. Lewin, Gainesville, FL (US); David C. Bloom, Gainesville, FL (US); Gregory S. Schultz, Gainesville, FL (US); Sonal Sanjeev Tuli, Gainesville, FL (US); Jia Liu, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 199 days.

(21) Appl. No.: 12/036,365

(22) Filed: Feb. 25, 2008

(65) Prior Publication Data

US 2009/0131644 A1    May 21, 2009

Related U.S. Application Data

(63) Continuation of application No. 10/808,042, filed on Mar. 24, 2004, now Pat. No. 7,335,763.

(60) Provisional application No. 60/457,279, filed on Mar. 25, 2003.

(51) Int. Cl.
*C07H 21/04*    (2006.01)

(52) U.S. Cl. .................................................. 536/24.5
(58) Field of Classification Search ................ 536/24.5
See application file for complete search history.

(56) References Cited

U.S. PATENT DOCUMENTS

| 6,277,621 | B1 | 8/2001 | Horsburgh et al. | |
| 2004/0077565 | A1* | 4/2004 | Pavco et al. | ............ 514/44 |
| 2005/0096282 | A1 | 5/2005 | Lewin et al. | |

FOREIGN PATENT DOCUMENTS

WO        WO 00/66780        * 11/2000

* cited by examiner

*Primary Examiner*—Brian Whiteman
(74) *Attorney, Agent, or Firm*—Timothy H. Van Dyke; Beusse Wolter Sanks Mora & Maire (57) ABSTRACT

Hammerhead ribozymes that target components critical to HSV replication (ICP4, $U_L20$, $U_L30$, and $U_L54$) were synthesized and shown to efficiently cleave target RNA encoding a portion of these components in in vitro assays. Several cloned cell lines stably expressing these ribozymes were established. HSV-mediated plaque formation was dramatically reduced in cells stably transfected with an anti-HSV ribozyme compared to non-transfected cells.

2 Claims, 4 Drawing Sheets

HERPESVIRUS RIBOZYMES AND VECTORS

CROSS-REFERENCE TO RELATED APPLICATIONS

The present application is a continuation in part of U.S. Ser. No. 10/808,042 filed Mar. 24, 2004, now issued as U.S. Pat. No. 7,335,763, which claims the priority of U.S. provisional patent application Ser. No. 60/457,279 filed Mar. 25, 2003, whose teachings are incorporated by reference.

FIELD OF THE INVENTION

This invention relates generally to the fields of molecular biology and medicine. More particularly, the invention relates to compositions and methods of controlling acute and recurrent viral infections using ribozymes that prevent viral replication by cleaving mRNAs encoding viral proteins.

BACKGROUND

Herpes simplex virus (HSV) is a nuclear replicating, icosahedral, enveloped DNA virus that can cause blisters and sores almost anywhere on the skin, usually around the mouth and nose, or on the genitals and buttocks. The sores associated with HSV infections may be painful and unsightly. For immunosuppressed patient and neonates, HSV infection can be serious and sometimes fatal.

HSV exists in two forms, HSV-1, which is usually associated with infections of the lips, mouth, and face, and, HSV-2, which is commonly associated with infections of the genitalia. Occasionally HSV can infect the eye, causing blindness in some cases. Although active HSV infections typically resolve without treatment, because HSV latently infects nerve cells, active infections tend to recur.

There is no known cure for HSV infection. Vaccines for preventing HSV infection in humans are not currently available. Conventional treatment of HSV infection is oral administration of anti-viral medications such as acyclovir, famciclovir, or valacyclovir. These are used to treat active outbreaks and to suppress recurrences. Although generally safe and effective, these drugs cannot eliminate a latent HSV infection.

Accordingly, what is needed is a new treatment modality that continuously produces antiviral agents that block replication of herpes-viruses in sensory neurons where they remain latent, diminishing the likelihood of viral reactivation. Such a new treatment modality could also protect against viral replication in the cornea, where recurrent infections lead to scarring and blindness.

SUMMARY

The invention relates to the development of ribozymes that can be used to treat HSV infections, as well as methods for producing and delivering such ribozymes. Hammerhead ribozymes that target components critical to HSV replication (ICP4, UL20, UL30, and UL54) were synthesized and shown to efficiently cleave target RNA encoding a portion of these components in in vitro assays. Several cloned cell lines stably expressing these ribozymes were established. HSV-mediated plaque formation was dramatically reduced in cells stably transfected with an anti-HSV ribozyme compared to non-transfected cells. The number of plaque forming units (pfu) was also significantly reduced in cultures transfected with an anti-HSV ribozyme compared to non-transfected cells. In cells transiently transfected with an anti-HSV ribozyme, target viral mRNA levels were much lower than in control cells. Thus, the ribozymes of the invention are also able to cleave target HSV mRNA and reduce virion production in living cells.

Accordingly, the invention features a ribozyme that specifically cleaves a target RNA sequence encoded by a HSV gene essential or important for efficient HSV replication or packaging. The gene can be, e.g., UL20, UL30, UL54, or ICP4. The ribozyme can be in a hammerhead configuration, within a vector, and/or within a cell. Examples of such ribozymes include those including SEQ ID NOs: 1, 3, 5, and/or 6.

In another aspect, the invention features a method for impairing HSV replication in a cell. This method includes the step of expressing in the cell, in an amount effective to reduce HSV replication in the cell, a ribozyme that specifically cleaves a target RNA sequence encoded by a HSV gene such as UL20, UL30, UL54, or ICP4.

The invention further includes a ribozyme-resistant cell for producing a HSV expression vector encoding an anti-HSV ribozyme. The cell includes at least one nucleotide sequence encoding a portion of an HSV gene, the nucleotide sequence having been modified to not be cleavable by the ribozyme.

Unless otherwise defined, all technical terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including any definitions will control. In addition, the particular embodiments discussed below are illustrative only and not intended to be limiting.

BRIEF DESCRIPTION OF THE DRAWINGS

FIG. 2 is an autoradiogram (A) and a graph (B) showing a time course of RNA target cleavage, and percentage of target cleaved, respectively, by ribozyme UL20-154.

DETAILED DESCRIPTION

The invention provides compositions and methods for inhibiting replication of HSV-1 and HSV-2 using ribozymes that cleave RNA targets encoded by the HSV genes UL20, UL30, UL54 and ICP4. Also provided are HSV expression vectors including nucleic acid sequences encoding ribozymes directed against RNA targets in these HSV genes, ribozyme-resistant cells useful for production and packaging of HSV viral vectors expressing HSV-targeting ribozymes, and methods for using such vectors to reduce HSV replication, e.g., in cells susceptible to recurrent HSV infection.

Biological Methods

Methods involving conventional molecular biology techniques are described herein. Such techniques are generally known in the art and are described in detail in methodology treatises such as Molecular Cloning: A Laboratory Manual, 3rd ed., vol. 1-3, ed. Sambrook et al., Cold Spring Harbor Laboratory Press, Cold Spring Harbor, N.Y., 2001; and Current Protocols in Molecular Biology, ed. Ausubel et al., Greene Publishing and Wiley-Interscience, New York, 1992 (with periodic updates).

HSV-Targeting Ribozymes

The invention provides ribozymes that specifically cleave a target RNA sequence encoded by an HSV gene essential for replication. The RNA targeted can be any that is essential or important for HSV replication, e.g., one that encodes a protein necessary for efficient genome replication or viral assembly. Exemplary targets include RNAs encoding UL20, UL30, UL54 and ICP4. To inhibit replication of HSV in a cell, ribozymes against 1, 2, 3, 4 or more such targets can be used. It is preferred that at least 2 or 3 different ribozymes be used simultaneously to prevent mutation rendering ribozyme resistance.

Several forms of naturally-occurring and synthetic ribozymes are known, including Group I and Group II introns, RNaseP, hairpin ribozymes and hammerhead ribozymes (Lewin A S and Hauswirth W W, Trends in Molecular Medicine 7: 221-228, 2001). Any form suitable for use in the invention might be used. For example, ribozymes of the invention can be in a hammerhead configuration.

Hammerhead ribozymes are advantageous because they can be engineered to selectively bind and cleave a complementary mRNA molecule, then release the fragments, repeating the process with the efficiency of a protein enzyme. As shown in examples below, they have proven to be highly effective at cleaving target RNA sequences selective for HSV-1 genes, including UL20, UL30, UL54 and ICP4. Because hammerhead ribozymes cleave after UX dinucleotides, where U represents uridine and where X can be any ribonucleotide except guanosine, specific target sequences should have this sequence. A large number are present in HSV RNA. In practice, NUX triplets (typically GUC, CUC or UUC) are required in the target mRNA. Such targets are used to design an antisense RNA of 12 or 13 nucleotides surrounding that site, but skipping the C, which does not form a conventional base pair with the ribozyme.

Preferred targets of the ribozymes of the invention are those RNA encoding HSV genes that include AUC, GUC, CUC or UUC triplets as these have proven to been the best substrates for cleavage by hammerhead ribozymes. The most preferred target RNAs include GUCUU or GUCUA as experiments performed using these as target have all proven successful except when the ribozyme folded incorrectly due to the remainder of the target sequence (i.e. base pairing between one of the "arms" of the ribozyme and the catalytic core of the ribozyme).

Figure 4:
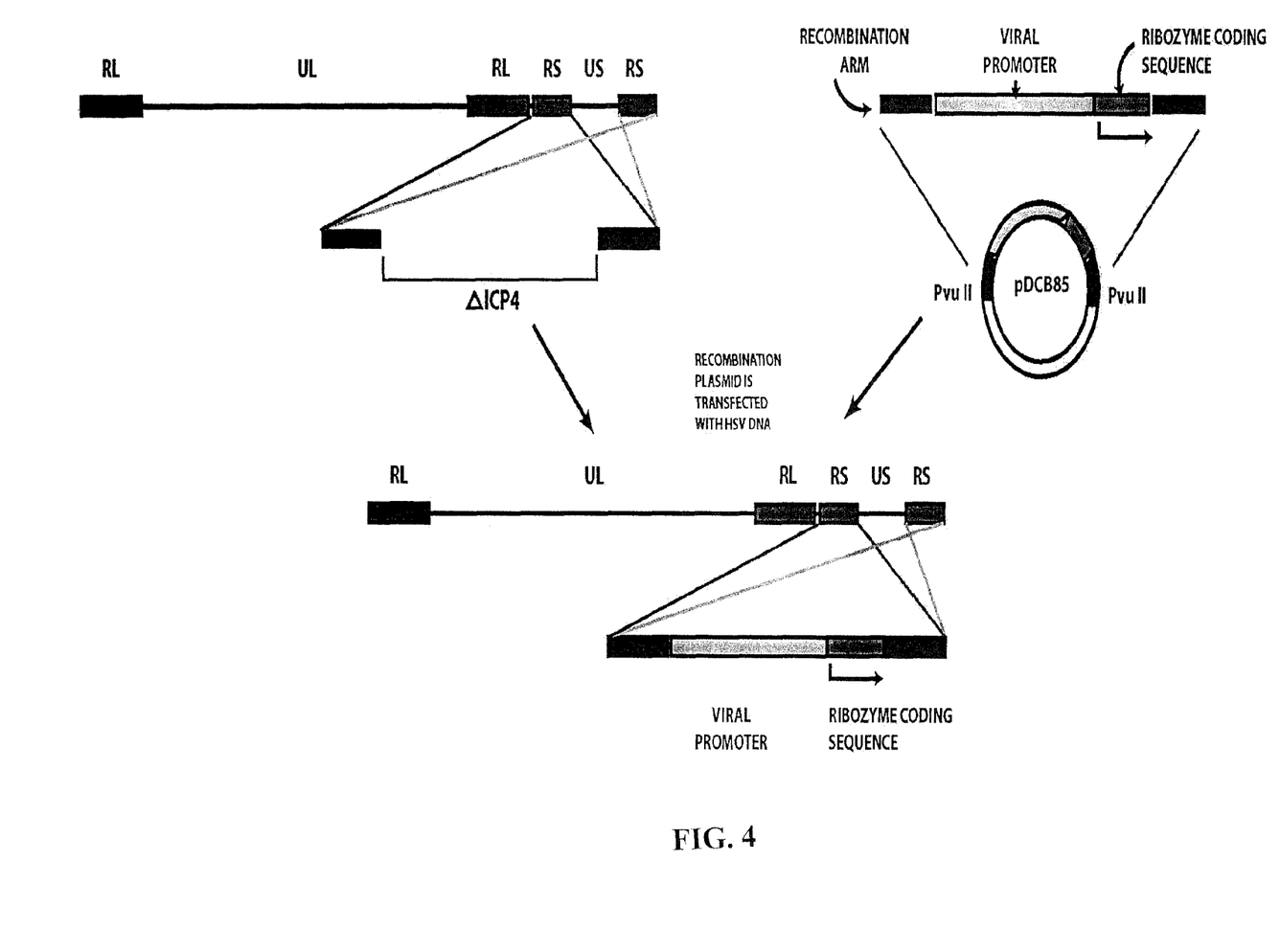
FIG. 4 is a highly schematic illustration of the construction of HSV-vectored ribozymes.

FIG. 4 shows examples of the design of several hammerhead ribozymes of the invention, aligned with the hammerhead portions of the molecules facing their respective RNA targets. Although each of these ribozymes is designed in a 6-4-5 stem-loop-stem configuration, any other configuration suitable for the purpose might be used. In general, because the chemical cleavage step is rapid and the release step is rate-limiting, speed and specificity are enhanced if the hybridizing "arms" of the ribozyme (helices I and III) are relatively short, e.g., about 5 or 6 nucleotides. Suitability of the design of a particular configuration can be determined empirically, using various assays as described below.

Secondary structure in RNA can interfere with the ability of a ribozyme to bind to the target site. For this reason, some synthetic ribozymes are more efficient than others at cleaving their targets. Structure-predicting algorithms such as MFOLD can be used to rule out certain target sites, but ultimately accessibility must be determined experimentally. To determine the cutting efficiency of a particular ribozyme, a series of in vitro tests can be performed as described in Shaw et al., Methods Enzymol. 316:761-776, 2000 and Fritz J J et al., Methods Enzymol. 346:358-377, 2002. In vitro screening of the kinetic properties of hammerhead ribozymes is recognized to be a cost-efficient analytic step, enabling selection of ribozymes having optimal cleavage characteristics without the necessity of more expensive animal studies. Details of screening methods for determining efficacy of the ribozymes of the invention, including assays of activity and multiple turnover kinetic analysis using short RNA targets and full length targets, as well as assays of the ability of ribozymes expressed in stably transfected cells to reduce HSV yields in HSV-infected cells, are further described in the examples below.

Vectors

Although the ribozymes of the invention might be used in naked nucleic acid form, to increase stability and expression, the invention further provides vectors for expressing a ribozyme of the invention. Any vector compatible with a particular application of the invention might be used. For example, plasmid or virus-based vectors might be used. Examples of virus-based vectors include those based on lentiviruses, other retroviruses, adenovirus, adeno-associated virus, foamy viruses, and herpes viruses. See, e.g., Kay et al., Nature Medicine 7:33-40, 2001.

For specifically targeting cells permissive to HSV infection, the ribozymes of the invention are preferably included in an HSV expression vector (e.g, a non-replicating HSV-based vector). HSV vectors expressing the anti-HSV RNA ribozymes can, for example, be based on a prototype vector, 8117/43, a non-replicating recombinant of HSV-1 that lacks the essential immediate early gene (i.e., ICP4) and contains the E. coli LacZ gene driven by a hybrid promoter. The promoter can be a fusion between the HSV latency associated transcript (LAT) promoter and the Moloney Murine Leukemia Virus long terminal repeat. Although this virus cannot productively replicate outside of a helper cell line, it is able to establish a latent infection within the peripheral and central nervous system of mice, rats and rabbits and humans. The hybrid promoter of this virus has been shown to be capable of expressing B-galactosidase for extended periods of time (Lokensgard J R et al., J Virol 68:7148-7158, 1994; Bloom D C et al., Gene Ther 1 Suppl 1:S36-S38, 1994).

To produce an HSV-based ribozyme-expressing vector, synthetic oligonucleotides encoding the ribozymes are cloned in a HSV recombination vector so as to place each ribozyme under the control of an HSV acute promoter. Any suitably constructed recombination plasmid can be utilized for this purpose, e.g., pDCB85 wherein the promoter-ribozyme cassette is flanked by the regions of the genome immediately upstream and downstream of the ICP4 promoter and coding region. These regions act as "recombination arms" that allow the promoter-ribozyme cassette to be inserted into the HSV-1 genome in place of ICP4 resulting in a replication-negative (i.e., ICP4-) HSV vector containing two copies of the promoter-ribozyme cassette, with one in each of the two short repeats. The recombination process is accomplished by co-transfecting virion DNA with the recombination plasmid into a helper cell line such as E5. Viral recombinants are subsequently identified, purified and characterized using known methods.

Ribozyme-Resistant Cell for Producing HSV-Vectored Ribozymes

The invention also provides a ribozyme-resistant cell for producing HSV-vectored ribozymes. In the case of a non-replicating HSV vector, e.g., one that is ICP4-, the vector can be propagated in a "helper" cell line (also known as a "complementing" or "packaging" cell line) that expresses the missing protein in trans. This can be achieved, e.g., using a cell line such as E5, which is based on Vero cells and expresses ICP4 (Shepard A A and DeLuca N A, J. Virol., 65:787-795, 1991). Nevertheless, those of skill in the art will recognize that any packaging cell line suitable for the purpose can be used.

The ribozyme-resistant packaging cell lines of the invention are designed to express a "hardened" version of the ribozyme target. Use of such cell lines is important because expression of an anti-HSV ribozyme in a packaging cell line would result in the production of ribozymes that inhibit viral replication and packaging. To avoid this, and thereby permit propagation of the ribozyme-expressing vectors, complementing cell lines can be constructed that produce their own "hardened" versions of the viral target mRNAs. Hardened versions of the targets are those that have been altered such that the ribozymes produced by the vector cannot cleave the targets (e.g., UL20, UL30, UL54 and ICP4) necessary for vector production within the packaging cell line.

Ribozyme-resistant cell lines can be made by introducing alterations into the coding sequences (e.g., silent mutations that change the nucleotide sequence but not the encoded amino acid sequence) of the target genes that make them resistant to the ribozymes using techniques such as site-directed mutagenesis. Complementing cell lines such as E5 cells (in the case of ICP4 targeting ribozymes) are then transfected with plasmids containing the mutagenized target genes. Those resulting cell lines exhibiting stable expression of the hardened targets are selected as packaging cell lines for producing vectors. Methods for producing mutagenized targets and their incorporation into cell lines are described in further detail in the examples below.

Stocks of ribozyme-expressing virus could also be prepared without the necessity of using a ribozyme-resistant packaging cell line constructed as described above, if, for example, a level of target mRNA production (e.g., resulting from the SV40 promoter in pZeoSV2) was achieved in the cell line sufficient to overcome cleavage by the ribozymes cloned into the non-replicating HSV vector.

Reducing HSV Replication in a Cell

The ribozymes of the invention can be used to prevent HSV replication in a cell as well as to prevent viral reactivation in latently infected cells by incorporating ribozymes directed against essential replicative genes of HSV into vectors capable of delivery of the ribozymes to the cell. The cell can be any cell type capable of infection by HSV, e.g. one actively or latently infected with the virus. Cell types particularly suitable for treatment with the ribozyme-targeting HSV vectors of the invention are cells of the nervous system, and affected tissues in contact with nerve endings (e.g., the cornea, conjunctiva, and mucosa) which are known to be susceptible to infection with HSV-1 or HSV-2.

EXAMPLES

Example 1

Hammerhead Ribozymes Targeting HSV mRNAs

1. Materials and Methods

Design of hammerhead ribozymes. Regions were selected in the target RNA containing NUX, where N represents any nucleotide, U represents uridine and X is any nucleotide except guanosine. Two stretches of antisense nucleotides that flank the conserved nucleotide sequence forming the catalytic domain between them were then designed, based on the target sequence surrounding the nucleotide X of the target. Nucleotide X was not base-paired with the ribozyme. The nucleotide sequences of each of the four HSV target genes (ICP4, UL20, UL30, UL54) were scanned for hammerhead cleavage sites (N-U-X) that were: 1) predicted to be in a single stranded region (not a base paired double stranded region) based on RNA folding programs (MFOLD 3.0) and 2) surrounded by flanking sequences that had a low G+C content. All ribozymes designed and tested employed a GUC target triplet, with the exception of human ICP4 Rz882, for which CUC was the target. To achieve highly active hammerhead ribozymes, helices I and III (which form the hammerhead portion of the ribozyme that is complementary to the target RNA sequence) were designed to contain no more than 12 base pairs.

Activity assays using short RNA targets. Ribozymes were synthesized and tested in vitro using end-labeled synthetic RNA oligonucleotides comprising the exact target sequence of the ribozyme. To ensure purity, both the RNA target and the ribozyme were gel purified prior to reaction, and the molar concentration of each was determined based on UV absorption. Denaturing gel electrophoresis was used to separate digestion products, and the extent of reaction was measured quantitatively using a Phosphorimager (Molecular Dynamics, Sunnyvale, Calif.).

Reaction time-course. Reaction time courses were evaluated under conditions consisting of 50-100 pmoles of target RNA in 10 mM $MgCl_2$, 40 mM Tris HCl, pH 7.5 (37° C.). After pre-incubation at 37° C., ribozyme was added at one tenth the concentration of substrate. Reaction aliquots were removed at intervals ranging from 1 minute to 2 hours for analysis of cleavage. Reactions were stopped by adding gel loading dye containing 95% formamide and 25 mM EDTA. Experimental conditions such as time of incubation, magnesium concentration, and ribozyme concentration were varied independently. Ribozymes requiring high magnesium concentrations or high ribozyme concentration for cleavage were eliminated from further consideration.

Multiple turnover kinetic analysis. Product release is frequently the rate-limiting step in ribozyme reactions. Therefore determining the activity of a particular ribozyme under substrate-excess (multiple turnover) conditions is often predictive of its utility in vivo. The appropriate interval for measuring reaction velocity was determined by a time-course experiment under multiple turnover conditions. Initial rates were measured when the amount of cleavage was linear with time, and when no more than 15% of substrate had been converted to product. Rates were measured at several intervals (e.g., 5, 10 and 20 min) to insure linearity. Samples were pre-incubated at 37° C. prior to initiation of cleavage, and contained 1-10 nM ribozyme and increasing concentrations of substrate RNA, while holding ribozyme concentration constant. Substrate concentrations greatly exceeded ribozyme concentration, this excess never being lower than 5-fold. Values for $V_{max}$ and $K_M$ were obtained by double reciprocal plots of velocity versus substrate concentration (Lineweaver-Burke plots) or by curve-fitting to the plot of [S] versus $V_0$. The turnover number $k_{cat}$ was determined by dividing $V_{max}$ by the ribozyme concentration.

Accessibility of the target site using full length targets. RNA assumes stable higher-order structures; accordingly, it must be determined that the target site for the ribozyme is accessible, e.g., that it is not internally base-paired within the mRNA. For this purpose, a secondary structure prediction (MFOLD) was first used, followed by experimental confirmation of accessibility.

For HSV-specific ribozymes, accessibility is tested by preparing clones of the desired cDNAs (e.g., ICP4, UL20, UL30 and UL54) in a T7 transcription vector (pT7/T3-19) using appropriate substrate DNA and primers. Run-off transcription is performed from each vector in the presence of $\alpha$.-$^{0.32}$P-UTP, and the concentration of each RNA product is determined by its specific radioactivity. Equimolar ribozyme and full length target RNA are incubated for increasing intervals as described above for oligonucleotide targets. Products of the reaction are separated on 5% polyacrylamide gels containing 8M urea as denaturant, and dried gels are analyzed using a Phosphorimager. Preferred ribozymes are those that cleave their cognate target mRNAs in this assay with desirable kinetic properties, i.e., with high percentage of full length target cleaved (e.g., >85% cleaved) and high turnover number using oligonucleotide targets ($k_{cat}$ that is substantially >1 min$^{-1}$).

2. Results

Figure 1:
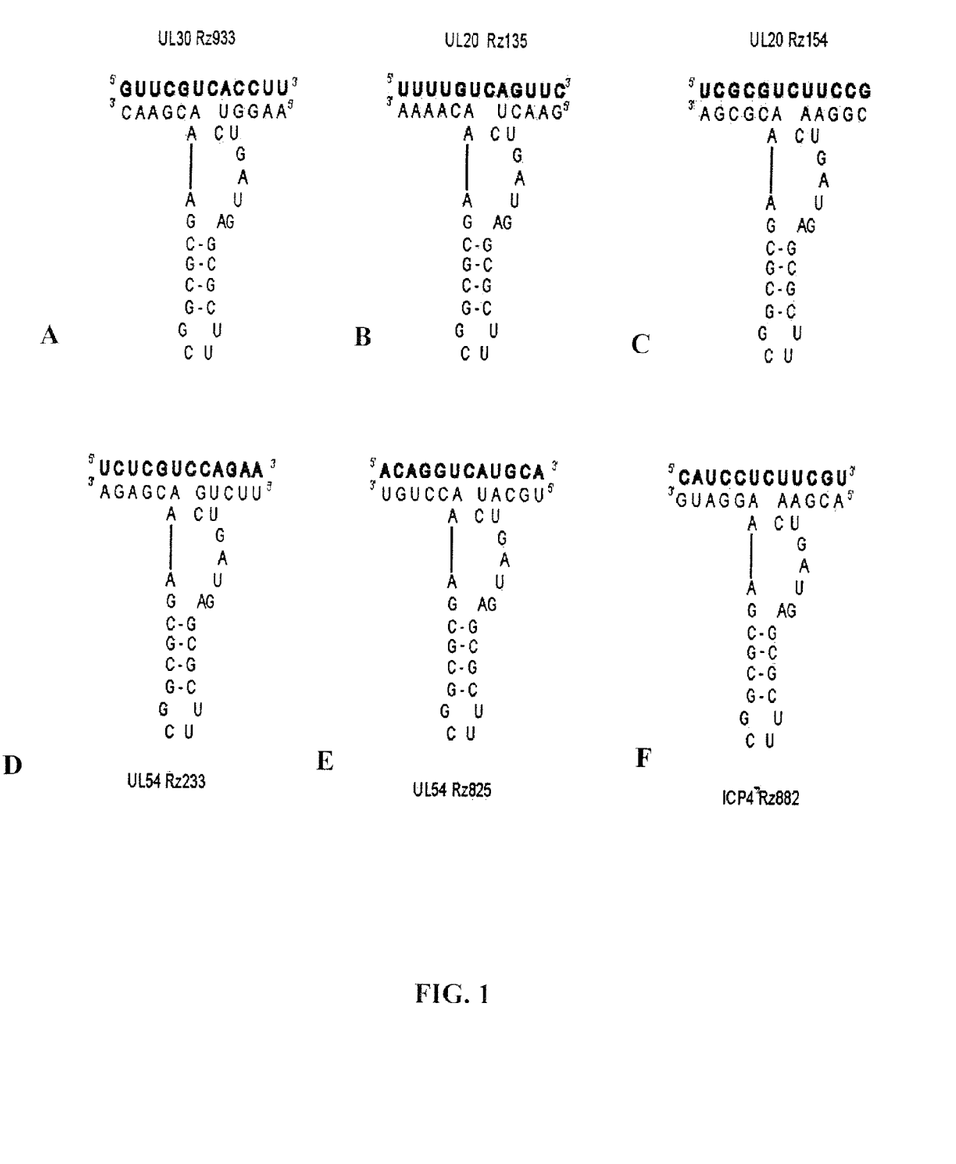
FIG. 1 is a diagram showing the RNA nucleotide sequences of ribozymes A.) SEQ ID NO. 1; B.) SEQ ID NO. 2; C.) SEQ ID NO. 3; D.) SEQ ID NO. 4; E.) SEQ ID NO. 5; and F.) SEQ ID NO. 6 directed against HSV genes UL20, UL30, UL54 and ICP4. The corresponding nucleotide sequences of the HSV target RNAs are indicated in boldface.

Using the above-described criteria, a large number of synthetic ribozymes was designed to cleave mRNAs from HSV genes UL20, UL30, UL54 and ICP4. FIGS. 1A-F show the nucleotide sequences of several exemplary ribozymes fitting the criteria. These synthetic ribozymes were all of the 6-4-5 stem-loop-stem design. The cleavage sites of five of the six depicted HSV target mRNAs were G-U-C sequences, whereas a C-U-C sequence was present in the ICP4-882 ribozyme (ICP4 Rz882) targeting ICP4 mRNA. The hammerhead portions (helices I, III) of the synthetic ribozymes is complementary to the listed sequences, except for replacement of thymidine (T) with uridine (U). The exemplary ribozymes, having the 6-4-5 stem-loop-stem design shown in FIGS. 1A-F, had the following RNA sequences:

```
                                          (SEQ ID NO: 1)
UL30Rz933:  5' AAG GUC UGA UGA GCG CUU CGG CGC GAA
ACG ACC 3'

(SEQ ID NO: 2)
UL20Rz135:  5' GAA CUC UGA UGA GCG CUU CGG CGC GAA
AGA AAA 3'

(SEQ ID NO: 3)
UL20Rz154:  5' CGG AAC UGA UGA GCG CGG CGC GAA ACG
CGA 3'

(SEQ ID NO: 4)
UL54Rz233:  5' UUC UGC UGA UGA GCG CUU CGG CGC GAA
ACG AGA 3'

(Seq ID NO: 5)
UL54Rz825:  5' UGC AUC UGA UGA GCG CUU CGG CGC GAA
ACC UGU 3'

(SEQ ID NO: 6)
ICP4Rz882:  5' ACG AAC UGA UGA GCG CUU CGG CGC GAA
AGG AUG 3'
```

Figure 2A:
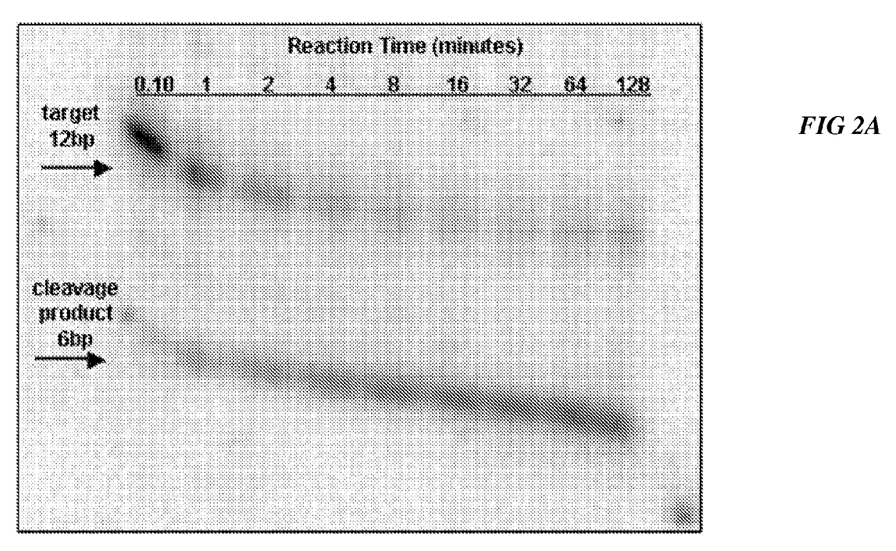
Figure 2B:
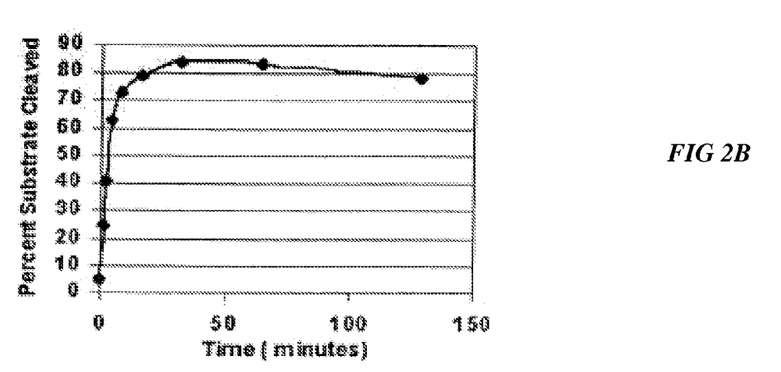

Activity assays and reaction time-course. RNA targets and ribozymes were chemically synthesized with perfectly complementary sequences, and the substrate targets were end-labeled with $^{32}$P-ATP. The test to assay activity was a time course to determine the rate at which the ribozymes cleaved the target and the percentage of target that was finally cut. FIG. 2A is an autoradiogram from a study of ribozyme UL20-154, showing the gradual disappearance of the target band (i.e., the 12 bp target) and concomitant appearance of increasing amounts of the resultant 6 bp cleavage product. Next, the percentage of substrate that was cut as a function of time was determined for a cleavage reaction with the same ribozyme, i.e., UL20-154. The results, shown in FIG. 2B, demonstrated high efficiency of this ribozyme, which cleaved more than 70% of the target within several minutes, and about 85% of the target within approximately 35 minutes.

TABLE 1

Kinetics Of Hammerhead Ribozymes With Synthetic HSV RNA

| HSV Target Gene | $Mg^{+2}$ mM | $k_{cat}$ (min$^{-1}$) | $K_m$ (um) | $k_{cat}/K_m$ (uM$^{-1}$ min$^{-1}$) |
|---|---|---|---|---|
| ICP4-581 | 20 | 15.9 | 52.8 | 0.301 |
| UL20-135 | 20 | 0.1 | 5.6 | 0.014 |
| UL20-154 | 5 | 27.8 | 1.8 | 15.886 |
| UL30-933 | 20 | 12.8 | 4.7 | 2.723 |
| UL54-825 | 5 | 51.3 | 4.4 | 11.659 |

Figure 3:
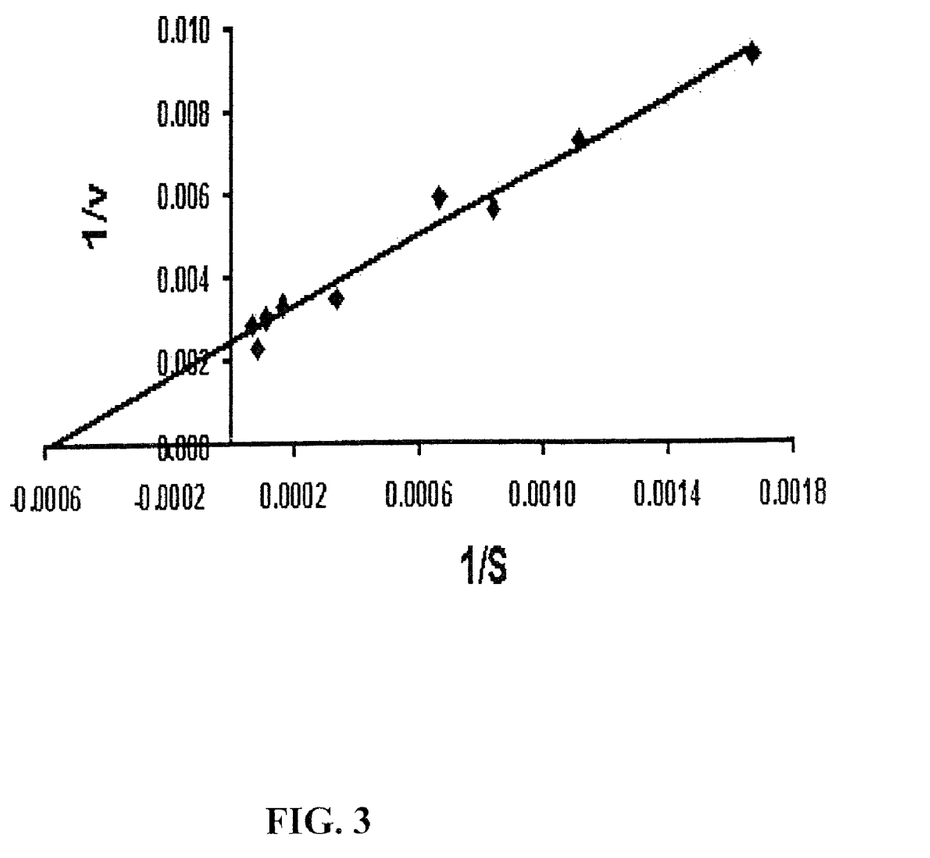
FIG. 3 is a graph showing a Lineweaver-Burke plot of ribozyme cleavage of a synthetic HSV RNA target. Least squares regression analysis generated a best fit line y=4.213+ 0.0024 with a correlation coefficient of $R^2 sup.2=0.978$.

Ribozyme activity under substrate-excess conditions. Activity of ribozymes was tested under substrate-excess conditions as described. The turnover number $k_{cat}$ was determined by dividing $V_{max}$ by the ribozyme concentration. FIG. 3 shows a typical Lineweaver-Burke plot for the UL20-154 ribozyme in 5 mM $Mg^{+2}$. Table 1 shows results of kinetic assays of five tested ribozymes (i.e., ICP4-581, UL20-154, UL30-933, UL54-825). Four of these demonstrated a $k_{cat}$ of substantially >1 min$^{-1}$, indicating very efficient cutting of their respective synthetic substrate RNAs. By contrast, an observed $k_{cat}$ value for the UL20-135 ribozyme of substantially <1 min$^{-1}$ indicated that this ribozyme was much less effective.

Example 2

Ribozyme-Mediated Inhibition of HSV Replication in Cultured Cells

Construction of stably transfected cell lines expressing the anti-HSV-1 ribozymes. Plasmids containing synthesized DNA templates encoding the ribozymes of the invention are constructed using the parent plasmid pTRUF21. This plasmid contains the ribozyme-coding sequence under the control of the CMV IE enhancer/chicken β.-globin hybrid promoter, and also contains the neomycin resistance gene in order to allow for selection of stable cell lines. Stably transfected Vero cells are constructed by transfecting semi-confluent monolayers in 60 mm dishes with the plasmids containing the ribozyme expression cassettes. The transfections are performed using Lipofectamine 2000 (Invitrogen, Carlsbad, Calif.) according to the manufacturer's recommendations. Following transfection, the cells are cultured in media containing 500 µg/ml G418 (Geneticin, InVitrogen), and several clonal lines of neomycin-resistant cells are isolated for each ribozyme construct, either by use of cloning cylinders or by limiting dilution. Following several passes of the lines, relative levels of ribozyme expression are assessed by QT-PCR. In addition to the cell lines expressing the ribozymes, a control cell line is used. The control cell line is constructed to contain the parent pTRUF21 plasmid with the CMV/chicken β.-actin promoter expressing green fluorescent protein (GFP).

Assay of the ability of the ribozymes to reduce HSV yields in infected cells. The ability of the ribozymes expressed by the stably transfected cell lines is assessed by performing single and multi-step viral replication assays on at least two separate cell lines for each ribozyme. All replication assays are performed in triplicate in 35 mm dishes containing just-confluent monolayers of each cell line. Assays include as controls the GFP-expressing cell line (and the parent Vero cell line). Infections are performed by removing media from the dishes and replacing with 0.3 ml of complete medium (Minimal Essential Medium, Gibco Life Technologies, Gaithersburg, Md., with 10% fetal bovine serum and antibiotics) containing wild-type HSV-1 strain 17syn+. This inoculum is allowed to adsorb onto the cells for 1 hour (at 37° C., 5% $CO_2$ with humidity), at which point it is removed and replaced with 2.5 ml complete medium. The dishes are then incubated (at 37° C., 5% $CO_2$ with humidity) for the appropriate time intervals, and harvested.

For single-step growth curve analysis, the cells are infected at a multiplicity of infection (m.o.i.) of 3, and dishes are harvested at 0, 4, 8, 12 and 18 hours post-infection. For multi-step growth analysis, the cells are infected at a m.o.i of 0.001, and dishes are harvested at 0, 4, 12, 24, 48, 72 and 96 hours post-infection. The method of harvesting can vary slightly, depending on the assay to be performed (described below).

Example 3

Ribozyme-Resistant Packaging Cell Line

Construction of packaging cell lines expressing "hardened" ribozyme targets. The ribozymes of the invention can be delivered to cells in an HSV vector. For example, the ribozymes can be delivered in a non-replicating HSV vector that contains a deletion in the ICP4 gene (Burton E A et al., Curr Opin Biotechnol 2002, 13:424-428). This vector can be propagated in the helper cell line E5. The E5 cell line is based on Vero cells, and has been engineered to contain the ICP4 gene stably integrated into its genome. To circumvent the problem of the HSV-targeting ribozyme cleaving the viral RNA needed for HSV vector propagation, a ribozyme-resistant E5 cell line is constructed that is capable of resisting the destructive effect of the ribozymes of the invention. To achieve this, E5 cells are transfected with plasmids containing the mutagenized target genes, following site-directed mutagenesis procedures described below. Stable cell lines demonstrating expression of the hardened target mRNAs are then selected for use as packaging cell lines.

Site-directed mutagenesis. Individual genes targeted by the ribozymes are cloned by PCR in plasmid pCR2.1 (Invitrogen, Carlsbad, Calif.) using HSV DNA as template, or by restriction-enzyme digestion and cloning directly into the pZeoSV2 expression plasmid. Nucleotide substitutions are introduced using a site-directed mutagenesis kit from Stratagene, which permits the co-conversion of several linked nucleotides. In the case of UL30, mutagenesis is performed on a SnaB1-Nhe1 restriction fragment of 778 nt, which is then recloned in the 3.7 kb reading frame. These sites are unique and flank the 5' region of the gene, in which several potential cleavage sites have been identified.

TABLE 2

Nucleotide Sequence of Wild-Type and "Hardened" RNA Targets for Ribozymes

| HSV mRNA | Wide-type target | "Hardened" target |
|---|---|---|
| ICP4 (position 882) | CAUCCUCUUCGU (SEQ ID NO: 7) | CUUCAUCCUCGU (SEQ ID NO: 8) |
| UL20 (position 135) | UUUUGUCAGUUC (SEQ ID NO: 9) | UUUCGUGAGCUC (SEQ ID NO. 10) |
| UL20 (Position 154) | UCGCGUCUUCCG (SEQ ID NO: 11) | UCACGCCUCCCG (SEQ ID NO: 12) |
| UL30 (position 933) | GUUCGUCACCUU (SEQ ID No: 3) | AUUCGUGACAUU (SEQ ID NO: 14) |
| UL54 (position 233) | UCUCGUCCAGAA (Sq. ID NO: 15) | UCCCGCCCCGAA (SEQ.D NO: 16) |
| UL54 (Position 825) | ACAGGUCAUGCA (SEQ. ID NO: 17) | ACAAGUGAUGCA (SEQ ID NO: 18) |

Example 4

HSV-Vectored Ribozymes

Construction of non-replicating HSV vectors. Non-replicating HSV vectors expressing the anti-HSV RNA ribozymes are constructed according to the strategy shown schematically in FIG. 4. The prototype of these vectors, 8117/43, is a non-replicating recombinant of HSV-1 that lacks the essential immediate early gene (ICP4) and contains the *E. coli* LacZ gene downstream of a hybrid promoter that is a fusion between the HSV LAT promoter and the Moloney Murine Leukemia Virus LTR. This vector has been shown to be capable of establishing a latent infection within the peripheral and central nervous systems of mice, rats and rabbits. Its hybrid promoter is capable of expressing β-galactosidase for extended periods of time (Lokensgard J R et al., J Virol 68:7148-7158, 1994; Bloom D C et al., Gene Ther 1 Suppl 1:S36-S38, 1994.)

To construct the ribozyme-expressing vectors, synthetic oligonucleotides encoding the ribozymes are cloned into the HSV recombination vector pDB85, so as to place each ribozyme under the control of an HSV acute promoter (FIG. 4). In plasmid pDB85, the promoter-ribozyme cassette is flanked by the region of the genome immediately upstream and downstream of the ICP4 promoter and coding region, and the cassette is inserted into the HSV-1 genome in place of ICP4. This results in an ICP4(−) HSV vector containing two copies of the promoter-ribozyme cassette (one in each of the two short repeats). The recombination process is accomplished by co-transfecting virion DNA with the recombination plasmid into the E5 helper cell line by calcium-phosphate precipitation. Viral recombinants are subsequently identified, purified and characterized as described (Bloom D C, in Methods in Molecular Biology, Herpes Simplex Protocols, Brown S and MacLean A, eds., Humana Press, 1998).

Growth, purification, and titration of the HSV recombinants for inoculation. The recombinant (ICP4-) HSV vectors are propagated on the appropriate "hardened" helper cell lines, prepared as described above. The HSV virions produced by the cell lines are purified from cellular debris by centrifugation through a gradient of, e.g., 5-15% Ficoll 4000 in PBS. This purification step is important because without it, cytopathology of producer cells can be seen when the non-replicating HSV mutants are used to infect cells in culture at high multiplicities of infection (m.o.i.>1). This result is thought to be largely due to the carry-over of cellular debris and viral peptides toxic to the cells at high concentration. Purification of the HSV vectors in the disclosed manner eliminates cytopathology at m.o.i. of less than 5. The viral band collected from the gradient is pelleted through PBS by ultracentrifugation, and the resulting pellet is resuspended in Modified Eagle's Medium (MEM) supplemented with 10% Fetal Bovine Serum (FBS), aliquoted and maintained at −80° C. An aliquot of each stock is titrated by standard techniques on E5 cells to determine the number of infectious particles present.

Example 5

Reduction of HSV-1 Replication by HSV-Vectored Ribozymes In Vitro

Following construction, characterization, and purification, HSV-ribozyme-expressing vectors can be analyzed for their ability to interfere with wild type (wt) HSV infection in vitro. In a typical assay, cultured epithelial cells of the skin are infected with the ribozyme-containing HSV vectors, and used to test the ability of these vectors to prevent or reduce viral replication following infection of the cells with wt HSV-1. Single-step and multi-step viral replication assays are performed essentially as described above, except that the non-replicating vectors are added to the cells at selected times in relation to the time of addition of the HSV-1, i.e., either prior to HSV infection, (e.g., 12 hours before), at the time of infection (co-infection with vector and HSV-1), or post-HSV-1 infection (e.g., 4 hours after). Performance of the replication assays in this manner allows assessment of both the capability of the vector-expressed ribozymes to interfere with HSV-1 infection and of the optimal time frame for action by the ribozymes.

Example 6

Reduction of HSV-1 Replication by HSV-Vectored Ribozymes In Vivo

This example describes an assay for testing the ability of HSV-vectored ribozymes of the invention to reduce the production of HSV-1 in a rabbit model of corneal infection (viral keratitis) caused by latent HSV infection in the trigeminal nerve. A latent infection of trigeminal nerves in rabbits can be established using established procedures (Shimomura Y et al., Invest Opthalmol Vis Sci 26:121-125, 1985). For example, the corneas of rabbits anesthetized by an intramuscular injection of ketamine and xylazine are scratched in a cross hatch pattern with a needle, then treated with a 25.mu.l inoculum containing $2 \times 10^5$ PFU of the 17 syn+ strain of HSV-1. This procedure results in clinical evidence of corneal inflammation and viral shedding in the tear film within 3-5 days in 100% of the animals. Viral shedding is confirmed by swabbing the conjunctiva with Dacron swabs which are swirled in medium, followed by determination of the viral number by PFU titration with rabbit epidermal cells. Observations including gradual resolution of the viral keratitis over the next 5 to 7 days, inability to detect viral particles in the tear film, and clearing of the cornea are indicative of latency of the virus in the trigeminal ganglion.

Latent HSV infection is reactivated experimentally in these animals by epinephrine iontophoresis. Briefly, rabbits are anesthetized with ketamine and xylazine. A 10 mm diameter Delrin eye cup with an 8 mm diameter internal well with a platinum electrode is placed on the cornea and the cathode electrode is attached to a shaved area of the rabbit's ear. The well is filled with a 0.01% epinephrine solution, and a direct current (0.8 mAmps, 7 Volts) is applied for 8 minutes. Within three days, clinical symptoms of HSV keratitis and viral shedding occur in approximately 80% of the eyes.

Following reactivation, the level of HSV shedding in the tears is measured using placing Schirmer strips (Allergan, Houston, Tex.) in the inferior cul-de-sac (Robert P Y et al., J Med Virol 66:506-511, 2002). Strips are applied to the lower formix and left long enough to wet the strips to 25 mm. The tear-soaked strips are cut into 5 mm pieces and immersed in a phosphate buffered saline solution. Lacrimal fluid residues are removed by heating in a microwave oven for 1 minute and incubating at room temperature for 2 hours. DNA is then extracted by matrix affinity chromatography using a QuiAmp blood kit (Qiagen, Courtaboeuf, France). PCR amplification of the extracted DNA is performed using quantitative Taq-Man PCR as described above.

Transduction of rabbit corneal and trigeminal cells with herpes-vectored ribozymes. Corneas of latently infected rabbits are injected intrastromally with 100.mu.l of saline containing the herpes-vectored ribozyme. Optimal numbers of infectious herpes vector particles for injection are expected to be in the range of $10^4$ to $10^6$ infectious vector particles, as determined using a reporter vector in varying concentrations. Injection is achieved, e.g., using a 30# hypodermic needle visualized under an operating microscope. Alternative methods of the vector infection include iontophoresis of the vector, collagen shield soaked in vector following scarification, and use of a suction trephine.

To test the ability of the herpes-vectored ribozymes to decrease or prevent the reactivation of HSV-1, rabbits are infected with the 17 syn+ strain of the virus on day 0. In this method, a large number of viral particles is generally shed in the tear film within 3-5 days following the infection, with viral shedding returning to baseline by 30 days post infection. On day 30, intrastromal injections of the herpes-vectored active ribozyme and two controls consisting of herpes-vectored inactive ribozyme and saline are performed. Seven days following the injection, when viral presence in the tears is minimal, epinephrine iontophoresis is used to reactivate the latent HSV-1 virus in the trigeminal ganglia, leading to viral shedding. The level of viral shedding in the tear film is measured starting 72 hours following the iontophoresis using PCR on Schirmer strips as described earlier, and results are analyzed comparing viral shedding observed in animals injected with control and herpes-vectored active ribozymes.

Example 7

Ribozyme-Mediated Reduction in Plaque Formation

Four cloned cell lines containing the ICP4-588 ribozyme, three cloned cell lines stably expressing the UL20-154 ribozyme, and two clones expressing the UL54-825 ribozyme were made. The ability of the ribozymes to reduce plaque formation was investigated. Briefly, immortalized rabbit epidermal skin cells (RS) that were stably transfected with the pTR-ICP4-588 ribozyme or non-transfected cells were cultured in 6 well plates to confluency then infected with HSV 17 syn+ virus at a MOI of 3:1. After 24 hours the plates were washed, fixed and stained to reveal plaques. Plaque formation in cultures of cells expressing the ribozymes was dramatically reduced compared to non-transfected cells as indicated by the nearly confluent lawn of blue staining cells. Furthermore, the number of plaque forming units (pfu) per culture was reduced approximately 90% as determined by titration of infectious virus extracted from the cell cultures 24 hours after infection. These results in stably transfected cells were supported by other results in E5 cells that were transiently transfected with a plasmid expressing the ICP4-581 ribozyme. An ethidium bromide-stained agar gel of RT-PCR reaction products showed an approximately 80% reduction in the level of ICP4 mRNA by the ribozyme compared to E5 cells that were transfected with the packaging vector without the ribozyme. In summary, these data show that the stable expression of the ICP4-588 ribozyme in RS cells results in an 8-fold reduction in infectious yield 24 hours after infection.

Example 8

Establishment of Latent HSV Infection and Reactivation in Rabbits

A latent infection in the trigeminal ganglion of rabbits was established by inoculating rabbit corneas with 25 µl of 2×10$^5$ pfu of the 17 syn+ strain of HSV 1. All 10 eyes of the five rabbits that were inoculated showed evidence of active epithelial and stromal infection within 4 days. This was confirmed by the presence of HSV DNA in conjunctival swabs. On resolution of the primary infection, the trigeminal ganglia of the rabbits was harvested and showed the presence of HSV DNA by PCR indicating the establishment of latent infection. Previous experiments by others using epinephrine iontophoresis on rabbits latently infected with the 17syn+ strain of HSV-1 showed a reactivation rate of almost 90%. In contrast, only 10% of the rabbits latently infected with the 17Δ Pst strain of HSV shed virus in their conjunctival sacs which is consistent with the known inefficient reactivation of this strain of HSV.

Example 9

Infection of Trigeminal Nerves in Rabbits by the HSV-LacZ Vector

Trigeminal neurons were infected with a Herpes vector by ocular instillation. β.-galactosidase activity, which is detected as blue reaction product, was present in numerous trigeminal neuron cell bodies and axons 72 hours following corneal intrastromal injection of the Herpes vector expressing LacZ reporter gene. This was confirmed in formalin-fixed, paraffin sections of the trigeminal nerve as seen in a Nomarski interference contrast photomicrograph. Numerous axons/dendrites which appeared as long streaks of blue stained segments were present, together with the large sensory neuron bodies. In addition, β.-galactosidase activity was present in the corneal limbal area. On histological examination, the β.-galactosidase activity was seen predominantly in the sub-epithelial stromal tissue in keratocytes. There was also some discrete punctuate staining in some epithelial cells. Similar staining patterns were seen in rabbits infected by placing the tagged Herpes vector in a suction ring placed on the cornea for 10 minutes.

Example 10

Reduction in Severity of a Herpes Simplex Virus Type I by Treatment with a Ribozyme Targeting the $U_L20$ Gene RNA Materials and Methods
Ribozyme kinetics in vitro. The inventors selected several genes as ribozyme targets based on their requirement for viral replication (MacLean, C. A., S. Efstathiou, M. L. Elliott, F. E. Jamieson, and D. J. McGeoch. 1991. Investigation of herpes simplex virus type 1 genes encoding multiply inserted membrane proteins. J Gen Virol 72 (Pt 4):897-906). Cleavage sites for hammerhead ribozymes were selected as previously described (Shaw, L. C., P. O. Whalen, K. A. Drenser, W. Yan, W. W. Hauswirth, and A. S. Lewin. 2000. Ribozymes in treatment of inherited retinal disease. Methods Enzymol 316: 761-76), and two ribozymes were tested for each target mRNA. Synthetic RNA oligonucleotides comprising hammerhead ribozymes and corresponding target sequences were purchased from Dharmacon, Inc (Lafayette, Colo.). The cleavage activity of each ribozyme was studied kinetically as described by Fritz et al (Fritz, J. J., D. A. White, A. S. Lewin, and W. W. Hauswirth. 2002. Designing and characterizing hammerhead ribozymes for use in AAV vector-mediated retinal gene therapies. Methods Enzymol 346:358-77).

Ribozyme cloning and packaging in adenoviral vector. Ribozymes were cloned in plasmid pAdlox (accession number R62024) for packaging into adenoviral vector. The hammerhead ribozyme was cloned between the CMV promoter sequence and the SV40 poly (A) signal. Following the hammerhead ribozyme we inserted a hairpin ribozyme that separates the antiviral hammerhead Rz from a downstream IRES-GFP element. The recombination method was previously published (10, 19). Adenoviral purification was conducted using Vivapure AdenoPACK™ 100 (Vivascience AG, Hannover, Germany). The virus particle concentration of adenovirus stock was measured as described by Plamer et al (Palmer, G. D., E. Gouze, J. N. Gouze, O. B. Betz, C. H. Evans, and S. C. Ghivizzani. 2003. Gene transfer to articular chondrocytes with recombinant adenovirus. Methods Mol Biol 215:235-46.). Two adenoviruses were used as controls in this study: ψ5 was the parental vector for transgene packaging, and Ad-GFP that expresses GFP from ψ5 backbone.

Herpes simplex virus type I (HSV-1) viral preparation. A low-passage stock of HSV-1 strain 17syn+ was prepared from a master stock obtained from Dr. J. Stevens (UCLA). Drug resistant strains of HSV-1, PAAr5 (Coen, D. M., and P. A. Schaffer. 1980. Two distinct loci confer resistance to acycloguanosine in herpes simplex virus type 1. Proc Natl Acad Sci USA 77:2265-9., Jacobson, J., M. Kramer, F. Rozenberg, A. Hu, and D. M. Coen. 1995. Synergistic effects on ganglionic herpes simplex virus infections by mutations or drugs that inhibit the viral polymerase and thymidine kinase. Virology 206:263-8), tkLTRZ1 (Jacobson, J. G., S. H. Chen, W. J. Cook, M. F. Kramer, and D. M. Coen. 1998. Importance of the herpes simplex virus UL24 gene for productive ganglionic infection in mice. Virology 242:161-9, Davar, G., M. F. Kramer, D. Garber, A. L. Roca, J. K. Andersen, W. Bebrin, C. D. M., M. Kosz-Vnenchak, D. M. Knipe, and X. O. Breakefield. 1994. Comparative efficacy of expression of genes delivered to mouse sensory neurons with herpes virus vectors. J. Comp. Neurol. 339:3-11) and ACG$^r$4 (Coen et al.) as well as their parental strain KOS were generously provided by Dr. D. Coen (Harvard Medical School). The HSV-1 virus was propagated and titrated on rabbit skin cells (RSC) grown in minimal essential medium supplemented with 5% calf serum and antibiotics (Tran, R. K., P. T. Lieu, S. Aguilar, E. K. Wagner, and D. C. Bloom. 2002. Altering the expression kinetics of VP5 results in altered virulence and pathogenesis of herpes simplex virus type 1 in mice. J. Virol 76:2199-2205.).

Ribozyme inhibition of multiple-step HSV-1 viral replication. All the infections were conducted in triplicate. Three groups were included to test effect of the ribozyme in a wild-type HSV-1 infection: mock treatment, ψ5 (backbone adenovirus), and Ad $U_L20$ Rz. Rabbit skin cells (RSC) were seeded at a density of $2\times10^5$ cells per well (3.5 cm$^2$) followed by adenoviral inoculation at a dose of $7.5\times10^4$ viral particles per cell for 15 hours. The infection of HSV-1 (17syn+) was conducted at an MOI of $10^{-3}$ for 24 hours before cell lysates were harvested for titration.

Four groups were included when testing the impact of the ribozyme on replication of drug resistant HSV-1 strains: mock infection and Ad-$U_L20$ Rz treatments were performed as before; an adenovirus expressing GFP was used instead of ψ5; and an acyclovir (ACV) treatment (0.1 μM) was included. The dosage of acyclovir was determined by the threshold dose needed to distinguish drug resistance of HSV-1 (Thi, T. N., C. Deback, I. Malet, P. Bonnafous, Z. Ait-Arkoub, and H. Agut. 2006. Rapid determination of antiviral drug susceptibility of herpes simplex virus types 1 and 2 by real-time PCR. Antiviral Res 69:152-7). Forty-eight hours were allowed for HSV-1 infection to develop before cell lysates were harvested for titration. Five HSV-1 strains were tested: 17syn+ and KOS are drug sensitive strains, and PAAr5, tkLTRZ1, and ACG′′4 are drug resistant isolates.

Ribozyme inhibition of $U_L20$ expression. We evaluated the effect of the $U_L20$ ribozyme on the one-step growth of HSV-1 (strain 17syn+). Each experiment was conducted in triplicate, and each included 3 treatments: mock infection, Ad-GFP, and Ad-$U_L20$ Rz. After inoculation of Ad-$U_L20$ Rz as described above, HSV-1 infection was conducted at an MOI of 3 for 8 hours before cell lysates were harvested using TriZol® reagent (Invitrogen, Carlsbad, Calif.). Total RNA and DNA were separated following the manufacturer's recommendation, and total RNA was treated with RNase-free DNase (Gorbatyuk, M., V. Justilien, J. Liu, W. W. Hauswirth, and A. S. Lewin. 2007. Preservation of photoreceptor morphology and function in P23H rats using an allele independent ribozyme. Exp Eye Res 84:44-52) to remove the DNA contamination. Reverse-transcription was conducted using First-Strand cDNA Synthesis Kit (Amersham Biosciences, Piscataway, N.J.) followed by Real-time PCR (Kubat, N. J., A. L. Amelio, N. V. Giordani, and D. C. Bloom. 2004. The Herpes Simplex Virus Type 1 Latency-Associated Transcript (LAT) Enhancer/rcr Is Hyperacetylated during Latency Independently of LAT Transcription. J Virol 78:12508-18). Specific primers and a fluorescent probe for either the viral gene or rabbit GAPDH (glyceraldehyde-3-phosphate dehydrogenase) were designed and synthesized by Applied Biosystems (Foster City, Calif.).

Testing ribozyme inhibition of HSV-1 encephalitis in mice. Six-week-old female Swiss Webster mice were used for this study, and the procedure of HSV-1 infection of mouse footpads described by Kubat et al.

Three groups of 10 mice were employed and two independent experiments were conducted. First, $1.4\times10^{10}$ viral particles of adenovirus (expressing either $U_L20$ Rz or GFP) or PBS in a volume of 10 μL per footpad was combined with 40 μL of 10% sterile saline solution and injected into both rear footpads. After 3 to 4 hours, mice were again inoculated with $1.4\times10^{10}$ viral particles of adenovirus ($U_L20$ Rz or GFP, respectively) or PBS topically on each rear footpad. This second application of adenovirus or PBS was followed by a topical application of HSV-1 (17syn+) at a dose of $10^4$ pfu per footpad.

Results

Kinetic analysis of HSV-1 ribozymes. Four essential HSV-1 genes were chosen as ribozyme targets, ICP4, $U_L20$, $U_L30$/DNA polymerase, and $U_L54$. Two ribozymes cleavage sites were selected for each gene, based on their moderate G+C content and predicted accessibility within the mRNA (Zuker, M. 2003. Mfold web server for nucleic acid folding and hybridization prediction. Nucleic Acids Res 31:3406-15).

Sequences of ribozymes and their cleavage sequences are shown in Table 3. Table 3. Ribozyme sequences and sequences of their respective targets.

| Ribozyme[†] | Ribozyme Sequence | Target Sequence |
|---|---|---|
| ICP4-885 | acgaactgatgagcgcttcggcgcgaaaggatg (SEQ ID NO: 20) | catcctcttcgt (SEQ ID NO: 21) |
| ICP4-533 | tcgatctgatgagcgcttcggcgcgaaacgccg (SEQ ID NO: 22) | cggcgtcatcga (SEQ ID NO: 23) |
| $U_L20$-135 | gaactctgatgagcgcttcggcgcgaaacaaaa (SEQ ID NO: 24) | ttttgtcagttc (SEQ ID NO: 25) |
| $U_L20$-154 | cggaactcatgagcgcttcggcgcgaaacgcga (SEQ ID NO: 26) | tcgcgtcttccg (SEQ ID NO: 27) |
| $U_L30$-933 | aaggtctgatgagcgcttcggcgcgaaacgaac (SEQ ID NO: 28) | gttcgtcaccttt (SEQ ID NO: 29) |
| $U_L30$-1092 | cacatctgatgagcgcttcggcgcgaaagcttg (SEQ ID NO: 30) | caagctcatgtg (SEQ ID NO: 31) |
| $U_L54$-233 | ttctgctgatgagcgcttcggcgcgaaacgaga (SEQ ID NO: 32) | tctcgtccagaa (SEQ ID NO: 33) |
| $U_L54$-825 | tgcatctgatgagcgcttcggcgcgaaacctgt (SEQ ID NO: 34) | acaggtcatgca (SEQ ID NO: 35) |

[†]Each ribozyme label includes the name of target gene (e.g., ICP4)

Ribozymes were evaluated for their catalytic efficiency using time-course and multiple-turnover kinetic analysis. The time course of cleavage was established at 10-fold excess substrate relative to ribozyme and at a $Mg^{2+}$ concentration of 5 mM, unless the rate of cleavage was low, in which case 20 mM $Mg^{2+}$ was also employed. The $U_L20$ Rz154, for example, led to 75% cleavage of its RNA target by 8 minutes low $Mg^{2+}$. The dependence of initial rates of cleavage on substrate concentration was then determined and analyzed using Lineweaver-Burke double reciprocal plots to determine $K_M$, $k_{cat}$ ($V_{Max}/[Rz]$), and $k_{cat}/K_M$. The value of $k_{cat}/K_M$, which is an estimate of catalytic efficiency, ranged from 0.01 for $U_L20$ Rz135 to 15.9 for $U_L20$ Rz154 (Table 4). For each HSV-1 target gene, the most efficient ribozyme was chosen for analysis of as an inhibitor of viral replication.

TABLE 4

Summary of in vitro kinetic analysis of hammerhead ribozymes designed against HSV-1. Kinetic Properties of Hammerhead Ribozymes with Synthetic HSV RNA Substrates

| HSV Target Gene | $Mg^{+2}$ mM | $k_{cat}$ ($min^{-1}$) | $K_m$ ($\mu M$) | $k_{cat}/K_m$ ($\mu M^{-1} min^{-1}$) |
|---|---|---|---|---|
| ICP4-885 | 20 | 15.87 | 52.83 | 0.3 |
| ICP4-533 | 5 & 20 | NA | NA | NA |
| $U_L20$-135 | 20 | 0.08 | 5.64 | 0.01 |
| $U_L20$-154 | 5 | 27.78 | 1.75 | 15.9 |
| $U_L30$-933 | 20 | 9.26 | 2.57 | 3.6 |
| $U_L30$-1092 | 5 | 22.99 | 23.59 | 1.0 |
| $U_L54$-233 | 5 | 0.91 | 8.58 | 0.1 |
| $U_L54$-825 | 5 | 51.28 | 4.44 | 11.7 |

Ribozyme targeting mRNA of HSV-1 $U_L20$ significantly reduced wild-type viral replication in rabbit skin cells. HSV-1 infection was conducted at a low MOI ($10^{-3}$) and the ribozyme was used to inhibit a multi-step HSV-1 viral replication. Ad-$U_L20$ Rz154 reduced HSV-1 wild-type viral replication by 83% compared with control treatment (ψ5) (p<0.001), and no significant difference was observed between no-treatment (no-Ad) and ψ5 treatments.

$U_L20$ ribozyme blocked the expression of $U_L20$ gene expression in vitro. Ad-$U_L20$ Rz154 was also tested in a one-step replication assay of HSV-1 following infection at an MOI of 3. As $U_L20$ is a late gene, an 8-hour incubation was used to allow completion of late gene expression. The effect of $U_L20$ Rz154 on $U_L20$ expression at the mRNA level was monitored by reverse-transcription followed by real-time PCR. A 68% reduction in $U_L20$ mRNA level was detected by comparing the Ad-ribozyme treatment with Ad-GFP treatment (p<0.0005). There was also a 50% reduction in $U_L20$ mRNA level using Ad-GFP treatment relative to mock infection (No-Ad) (p<0.0004). It is therefore likely that pre-infection of the cells with adenoviral vectors, reduces the replication of HSV-1. DNA was also extracted from each infection sample, and viral DNA level normalized to the endogenous cellular control (GAPDH) were also determined using real-time PCR. A 54% reduction in viral DNA levels was also observed in the ribozyme treatment group compared with the Ad-GFP group (p<0.004), but there was no significant difference between the mock infection and the Ad-GFP treatments with respect to viral DNA levels.

$U_L20$-Rz154 inhibits viral replication of HSV-1 drug resistant strains. Ad-$U_L20$ Rz154 was compared with acyclovir treatment in a multi-step infection at an MOI of $10^{-3}$. $U_L20$-Rz154 significantly inhibited wild-type HSV-1 viral production (by 98% against 17syn+ and by 95% against KOS strains), and acyclovir treatment led to a similar level of inhibition (by 99% and 80%, respectively). However, acyclovir treatment was not effective in drug-resistant strains of HSV-1 (no significant difference in HSV yields), while $U_L20$ ribozyme maintained its inhibitory effect. In the case of PAAr5 infection, $U_L20$ ribozyme reduced viral production by 99%; against tkLTRZ1 infection, it reduced virus yield by 76%; and against ACGr4 by 70%. Therefore, knocking down the expression of the $U_L20$ gene led to a significant inhibition of HSV-1 viral replication in viral strains that were resistant to a conventional antiviral drug.

$U_L20$ ribozyme protected mice from footpad infection of lethal dose of HSV-1. To evaluate the impact of blocking the expression of $U_L20$ gene in vivo, Ad-$U_L20$ Rz154 was delivered to mouse footpad before infection using a lethal dose of HSV-1 ($10^4$ pfu of 17syn+ per footpad). $1.4 \times 10^{10}$ viral Ad particles (expressing either $U_L20$-Rz154 or GFP) injected into both rear footpads. Three hours later, mice were challenged with HSV-1. With the ribozyme treatment, 89% of animals survived, while 45% and 40% survival rate were observed in PBS and GFP treated controls, respectively. Kruskal-Wallis non-parametric analysis showed a significant difference among the three groups (p=0.04). Beginning from the $6^{th}$ day after HSV-1 infection, mice from control groups (GFP and PBS treatments) showed signs of encephalitis, including hind-limb paralysis, hunched posture, ruffled fur, ataxia, and weakness. However, mice from ribozyme treatment group remained healthy and active, although two deaths were observed and one mouse showed mild paralysis in one hind limb in a much later time-point (data not shown).

To further investigate the impact of ribozyme effect on viral replication in vivo, an independent experiment was performed that at 4 or 6 hours after HSV-1 infection, four mice per group (ribozyme or GFP control treatment) were sacrificed to collect various tissues (feet, dorsal root ganglia, and spinal cord). Real-time PCR was conducted to compare viral DNA level from different tissues. With ribozyme treatment less HSV-1 viral DNA was recovered from all the tissues at each time point, but this trend did not achieve statistical significance (data not shown).

Other Embodiments

While the above specification contains many specifics, these should not be construed as limitations on the scope of the invention, but rather as examples of preferred embodiments thereof. Many other variations are possible.

The disclosure of all references, including related patents or patent applications cited herein are incorporated by reference to the extent not inconsistent with the teachings herein.

What is claimed is:

1. A ribozyme that specifically cleaves a target RNA sequence encoded by a HSV gene, wherein said ribozyme comprising the nucleotide sequence set forth in SEQ ID NO 5.

2. The ribozyme of claim 1, wherein said ribozyme targets a sequence set forth in SEQ ID NO. 7.

* * * * *

SEQUENCE LISTING

<160> NUMBER OF SEQ ID NOS: 18

<210> SEQ ID NO 1
<211> LENGTH: 33
<212> TYPE: RNA
<213> ORGANISM: ARTIFICIAL
<220> FEATURE:

<223> OTHER INFORMATION: synthetic ribozyme

<400> SEQUENCE: 1
aaggucugau gagcgcuucg gcgcgaaacg aac             33

<210> SEQ ID NO 2
<211> LENGTH: 33
<212> TYPE: RNA
<213> ORGANISM: ARTIFICIAL
<220> FEATURE:
<223> OTHER INFORMATION: synthetic ribozyme

<400> SEQUENCE: 2
gaacucugau gagcgcuucg gcgcgaaaca aaa             33

<210> SEQ ID NO 3
<211> LENGTH: 33
<212> TYPE: RNA
<213> ORGANISM: ARTIFICIAL
<220> FEATURE:
<223> OTHER INFORMATION: synthetic ribozyme

<400> SEQUENCE: 3
cggaacugau gagcgcuucg gcgcgaaacg cga             33

<210> SEQ ID NO 4
<211> LENGTH: 33
<212> TYPE: RNA
<213> ORGANISM: ARTIFICIAL
<220> FEATURE:
<223> OTHER INFORMATION: synthetic ribozyme

<400> SEQUENCE: 4
uucugcugau gagcgcuucg gcgcgaaacg aga             33

<210> SEQ ID NO 5
<211> LENGTH: 33
<212> TYPE: RNA
<213> ORGANISM: ARTIFICIAL
<220> FEATURE:
<223> OTHER INFORMATION: synthetic ribozyme

<400> SEQUENCE: 5
ugcaucugau gagcgcuucg gcgcgaaacc ugu             33

<210> SEQ ID NO 6
<211> LENGTH: 33
<212> TYPE: RNA
<213> ORGANISM: ARTIFICIAL
<220> FEATURE:
<223> OTHER INFORMATION: synthetic ribozyme

<400> SEQUENCE: 6
acgaacugau gagcgcuucg gcgcgaaagg aug             33

<210> SEQ ID NO 7
<211> LENGTH: 12
<212> TYPE: RNA
<213> ORGANISM: HERPES SIMPLEX VIRUS

<400> SEQUENCE: 7
cauccucuuc gu             12

<210> SEQ ID NO 8
<211> LENGTH: 12

```
<212> TYPE: RNA
<213> ORGANISM: ARTIFICIAL
<220> FEATURE:
<223> OTHER INFORMATION: synthetic sequence containing site-directed
      mutations

<400> SEQUENCE: 8
cuucauccuc gu                                                          12

<210> SEQ ID NO 9
<211> LENGTH: 12
<212> TYPE: RNA
<213> ORGANISM: HERPES SIMPLEX VIRUS

<400> SEQUENCE: 9
uuuugucagu uc                                                          12

<210> SEQ ID NO 10
<211> LENGTH: 12
<212> TYPE: RNA
<213> ORGANISM: ARTIFICIAL
<220> FEATURE:
<223> OTHER INFORMATION: synthetic sequence containing site-directed
      mutations

<400> SEQUENCE: 10
uuucgugagc uc                                                          12

<210> SEQ ID NO 11
<211> LENGTH: 12
<212> TYPE: RNA
<213> ORGANISM: HERPES SIMPLEX VIRUS

<400> SEQUENCE: 11
ucgcgucuuc cg                                                          12

<210> SEQ ID NO 12
<211> LENGTH: 12
<212> TYPE: RNA
<213> ORGANISM: ARTIFICIAL
<220> FEATURE:
<223> OTHER INFORMATION: synthetic sequence containing site-directed
      mutations

<400> SEQUENCE: 12
ucacgccucc cg                                                          12

<210> SEQ ID NO 13
<211> LENGTH: 12
<212> TYPE: RNA
<213> ORGANISM: HERPES SIMPLEX VIRUS

<400> SEQUENCE: 13
guucgucacc uu                                                          12

<210> SEQ ID NO 14
<211> LENGTH: 12
<212> TYPE: RNA
<213> ORGANISM: ARTIFICIAL
<220> FEATURE:
<223> OTHER INFORMATION: synthetic sequence containing site-directed
      mutations

<400> SEQUENCE: 14
auucgugaca uu                                                          12
```

-continued

```
<210> SEQ ID NO 15
<211> LENGTH: 12
<212> TYPE: RNA
<213> ORGANISM: HERPES SIMPLEX VIRUS

<400> SEQUENCE: 15
ucucguccag aa                                                         12

<210> SEQ ID NO 16
<211> LENGTH: 12
<212> TYPE: RNA
<213> ORGANISM: ARTIFICIAL
<220> FEATURE:
<223> OTHER INFORMATION: synthetic sequence containing site-directed
      mutations
<400> SEQUENCE: 16
ucccgccccg aa                                                         12

<210> SEQ ID NO 17
<211> LENGTH: 12
<212> TYPE: RNA
<213> ORGANISM: HERPES SIMPLEX VIRUS

<400> SEQUENCE: 17
acaggucaug ca                                                         12

<210> SEQ ID NO 18
<211> LENGTH: 12
<212> TYPE: RNA
<213> ORGANISM: ARTIFICIAL
<220> FEATURE:
<223> OTHER INFORMATION: synthetic sequence containing site-directed
      mutations
<400> SEQUENCE: 18
acaagugaug ca                                                         12
```